United States Patent [19]

Hommann

[11] Patent Number: 4,585,415
[45] Date of Patent: Apr. 29, 1986

[54] MOUTH AND TOOTH SPRAY APPARATUS

[75] Inventor: Edgar Hommann, Grossaffoltern, Switzerland

[73] Assignee: Gimelli & Co. AG, Switzerland

[21] Appl. No.: 597,840

[22] Filed: Apr. 9, 1984

[30] Foreign Application Priority Data

Apr. 7, 1983 [DE] Fed. Rep. of Germany ....... 3312451

[51] Int. Cl.$^4$ ............................................. A61C 17/02
[52] U.S. Cl. ...................................... 433/80; 604/152; 128/62 A
[58] Field of Search ..................... 128/66, 62 R, 62 A; 417/115; 604/152; 433/80

[56] References Cited

U.S. PATENT DOCUMENTS 3,393,673  7/1968  Mattingly .............................. 604/152

Primary Examiner—Robert Peshock
Attorney, Agent, or Firm—Wegner & Bretschneider

[57] ABSTRACT

In a mouth and tooth spray apparatus, a handle is mounted in a mounting such that the handle can be pivoted out of an upright position about an axis into a horizontal position parallel to the long wall of the appliance base of the mouth and tooth spray apparatus. This design makes it possible to push the water container, as a cover, over the appliance base from the narrow side of the appliance base.

7 Claims, 3 Drawing Figures

MOUTH AND TOOTH SPRAY APPARATUS

BACKGROUND OF THE INVENTION

This invention relates to a mouth and tooth spray apparatus with an appliance base in which is arranged a mounting with a detachably fastened handle for a spray nozzle, and which has a water container which can alternatively be set on the appliance base or can be put over the appliance base as a cover. A mouth and tooth spray apparatus of this kind is described in European Patent Application No. 0029636.

In the known mouth and tooth spray apparatus, the water container, for transportation, is put over the side of the appliance base which is in front during use, i.e., the wide side. In this way the mouth and tooth spray apparatus can be placed in a relatively compact state for travel. For transportation, of course, the handle with its water tube has to be detached from the appliance base. For this purpose, the mounting of the handle is provided with a coupling piece with which it can be plugged into and received in the appliance base. Both this handle with the coupling piece and also the various spray nozzles have to be transported separately, in the known mouth and tooth spray apparatus, which is impractical and can lead to damage or even loss of these components.

It is already known from U.S. Pat. No. 3,393,673 to make the mounting to the handle displaceable in a mouth and tooth spray apparatus, so that the mounting can be pushed into the appliance base for transportation. However, since the handle is always held upright in the mounting, a relatively large space must be provided in the cover, i.e., in the inverted water container, so that there can be room for the handle under the cover.

SUMMARY OF THE INVENTION

The primary object of the present invention is to create a mouth and tooth spray apparatus such that the handle can remain in its mounting in the appliance base for transportation, without the need for an undesirable large space for storing the handle.

This object is achieved according to the invention in that the mounting for the handle is made pivotable, and the appliance base has a free space to receive the handle carried by the mounting and pivoted into a horizontal position.

The main advantage of the invention is that in a mouth and tooth spray apparatus according to the invention, in order to push the cover on, the handle located in the mounting has only to be turned down. The tube of the handle can always remain connected to the pump outlet. The mouth and tooth spray apparatus according to the invention is thus very easy to bring into its operating position after transportation, or vice versa, to close for transportation after use.

Since the handle always remains in the appliance base during transportation, it is protected from damage and loss. Because of the possibility of turning the handle down, the water container acting as a cover can be constructed as a component to be closely inverted over the appliance base, so that the mouth and tooth spray apparatus is very compact in its closed transportation state.

A particularly simple construction is provided in one embodiment of the mouth and tooth spray apparatus wherein the mounting is provided on a narrow side of the appliance base and is pivotable about an axis running parallel to the narrow side, and the free space is correspondingly located on a long side of the appliance base.

It is advantageous for manipulation if the mounting is provided on the free end face of a winding body, held cantilevered on a base surface, for the water tube of the handle. The water tube is usually wound up in a coil and can slip back by itself, because of its inherent elasticity, after use of the mouth and tooth spray apparatus.

Various spray nozzles can likewise be transported with saving of space and secured against loss and damage, if according to another embodiment of the invention the winding body is constructed as a hollow body for storage of various spray nozzles.

When the appliance base is as wide as the container is long and as high as the water container is wide such that when the water container is put on, the winding body is located in front of, and the free space is located near the water container, the water container causes no problems when the water tube is pushed on and when the handle is gripped or put down.

Spray nozzles not in use are always handy for use if receptacles are provided in the base surface of the free space, for vertical storage of spray nozzles not in use.

If the appliance base of the mouth and tooth spray apparatus has on its rear side a receiving part for pushing the appliance base onto a wall bracket, and has on its narrow side opposite the winding body a wall bracket identical to the wall bracket, for pushing on a toothbrush charging appliance, it is then possible to fasten on a wall bracket, which is mounted firmly on a wall, either a toothbrush charging appliance or else the appliance base of the mouth and tooth spray apparatus. The toothbrush charging appliance can also be attached to the appliance base, so that only one wall bracket has be fastened to the wall.

It is advantageous if the drive of the water pump takes place by means of an electric toothbrush, which is to be placed upside down in a receptacle of the appliance base. In such an embodiment, no pump drive is required in the appliance base. The appliance base is hence of particularly small construction and has a low weight, which is appropriate for transportation during travel.

BRIEF DESCRIPTION OF THE DRAWINGS

Numerous embodiments of the invention are possible. One embodiment is described below and shown in the drawings wherein.

DESCRIPTION OF THE PREFERRED EMBODIMENT

Figure 1:
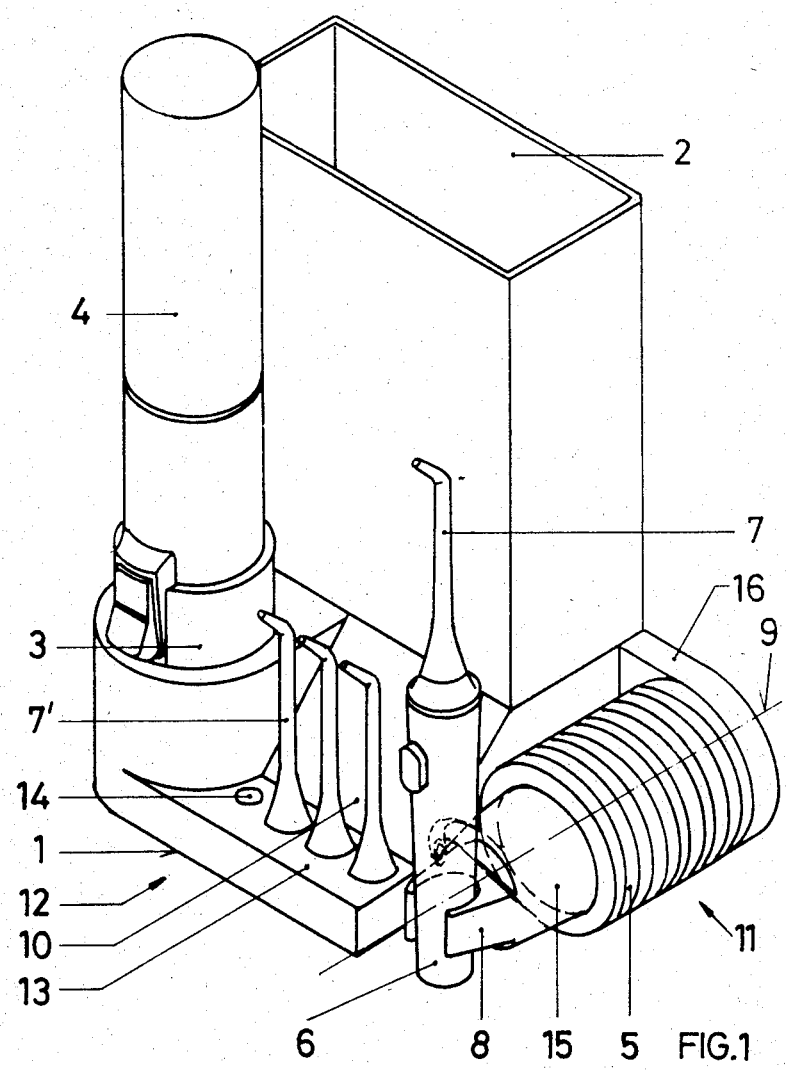
FIG. 1 is a perspective view of a mouth and tooth spray apparatus according to the invention, seen obliquely from the front.

The mouth and tooth spray apparatus shown in FIG. 1 has an appliance base 1, on which stands a water container 2 which is open at the top. Upside down in a receptacle 3 of the appliance base 1 there stands an electric toothbrush 4 which, by means of its drive spindle (not shown), drives a pump (likewise not shown) in the interior of the appliance base 1. During operation of the mouth and spray apparatus, this pump transfers water from the water container 2 via a tube 5 through a handle 6 and out of a spray nozzle 7.

The handle 6 rests in a mounting 8, out of which it can be taken for use. This mounting 8 is pivotable about an axis 9 such that the handle comes to rest, in a position which is pivoted through 90 degrees with respect to the position shown, in a free space between an inclined wall 10 of the appliance base and base surface 13. For this purpose, the axis 9 runs parallel to the front narrow side 11 and the free space near inclined wall 10 is parallel to the wide side 12 of the appliance base 1. Receptacles 14 are located in the base surface 13, and the various spray nozzles 7' are placed in them. FIG. 1 furthermore shows that the mounting 8 is fastened to the free end face of a winding body 15 which at its other end face is mounted cantilevered on a bracket 16 of the appliance base 1.

Figure 2:
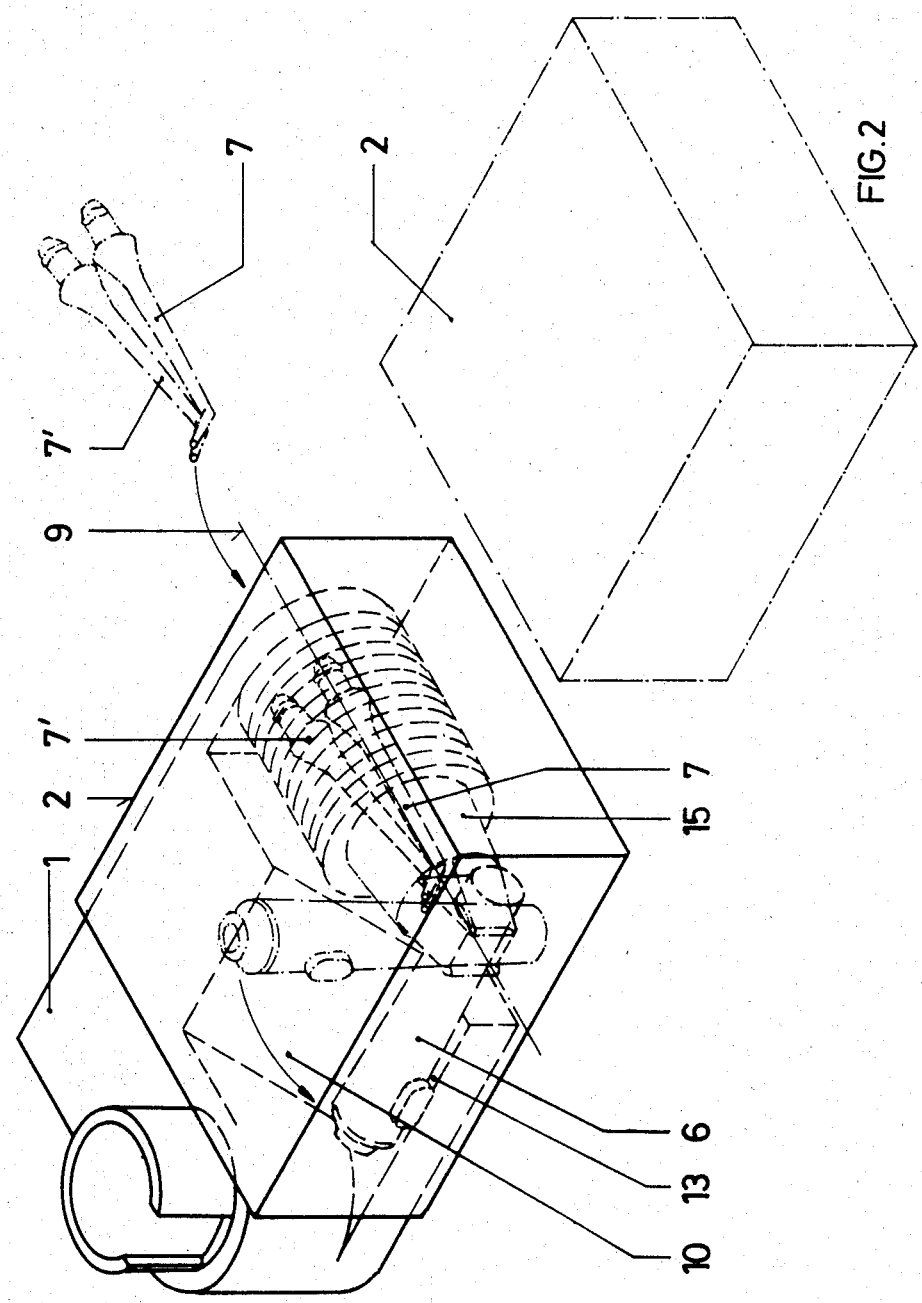
FIG. 2 is a perspective view of the mouth and tooth spray apparatus according to FIG. 1 in the transportation position, i.e., in a position in which its water container is pushed as a cover over the appliance base.

FIG. 2 shows the mouth and spray appliance in the closed state. For this, the spray nozzles 7' are first removed from the base surface 13. The handle 6 is then pivoted about the shaft 9 until the handle abuts the base surface 13. The winding body 15 is constructed, according to the invention, as a hollow body, so that the spray nozzles 7, 7' can find space in the winding body 15, as shown by dashed lines. When the spray nozzles 7, 7' are stored in the winding body 15 and the handle 6 has been turned down, the water container 2 can be pushed from the narrow side 11 over the appliance base 1. The water container 2 is shown in dot-dash lines in FIG. 2, before being pushed onto the appliance base 1.

Figure 3:
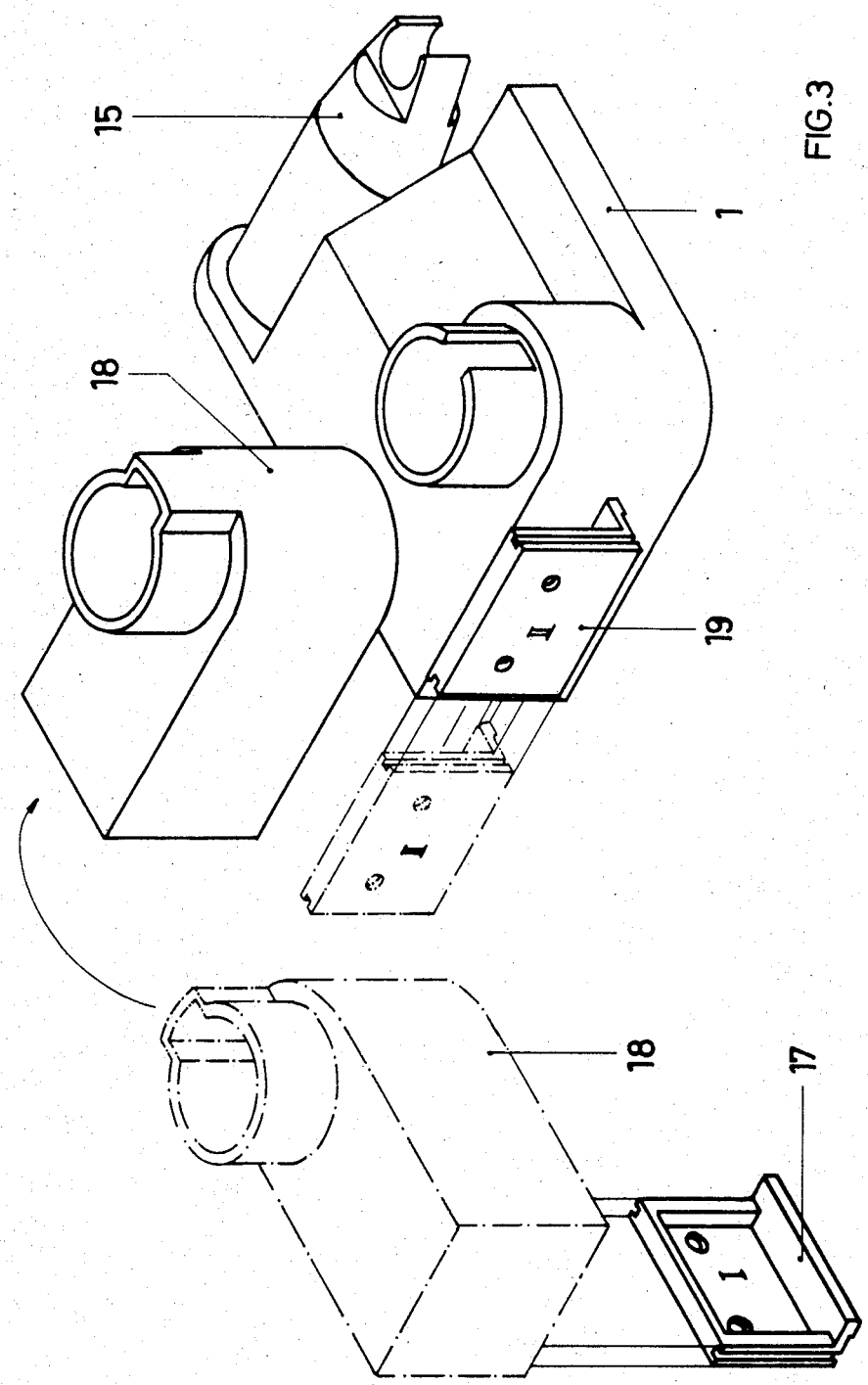
FIG. 3 is a diagrammatic perspective representation of the mouth and tooth spray apparatus and of a toothbrush charging appliance with mountings to connect the appliances together and to a wall.

FIG. 3 shows a stationary wall bracket 17, fastened to a wall, e.g. with screws, and onto which a toothbrush charging appliance 18 is to be pushed by means of a receiving piece (not shown), so that the toothbrush charging appliance 18 can be held on the wall. The appliance base 1 of the mouth and tooth spray apparatus has a corresponding receiving part (not shown) on its rear side, by means of which part the appliance base 1 can be attached to the wall holder 17 instead of the toothbrush charging appliance 18. Furthermore, the appliance base 1 has on its narrow side opposite the winding body a wall bracket 19 matching the wall bracket 17. Hence the toothbrush charging appliance 18 can be attached alternatively to the wall bracket 19 instead of to the wall bracket 17. In this way, the toothbrush charging appliance 17 and the appliance base 1 can be connected together. The unit formed in this manner can then be fastened to the wall bracket 17, the appliance base 1 being pushed with its receiving part on its rear side over the wall bracket 17.

Finally, it is to be remarked that as a modification of the embodiment shown, the winding body 15 can also be located in front of the toothbrush 4 in the appliance base 1. The free space would then have to be where the winding body 15 is located in the described embodiment. In this embodiment, the handle would fold rearward about an axis running parallel to the front long side.

Instead of the electric toothbrush 4, the water pump of the mouth and tooth spray apparatus according to the invention can, of course, also be driven by means of an internally fitted motor, as is conventional.

I claim:

1. A mouth and tooth spray apparatus comprising:
   (A) an elongated base;
   (B) a handle for holding a nozzle to spray fluid therefrom;
   (C) mounting means for holding said handle when not in use, said mounting means being mounted at one end of said base and rotatable about an axis parallel to said end between a first position where said handle is disposed essentially vertically when ready for use and a second position where said handle is disposed essentially horizontally to lie in a free space on said base along one side thereof when not in use; and
   (D) a fluid container adapted to be mounted on said base to supply fluid to said handle and, when empty, to be placed over said base as a cover.

2. Mouth and tooth spray apparatus according to claim 1, further comprising a tube for supplying water to the handle, and a winding body for the water tube held cantilevered on the base surface, wherein said mounting means is provided on a free end face of the winding body.

3. Mouth and tooth spray apparatus according to claim 2 wherein the winding body is constructed as a hollow body for storage of various spray nozzles.

4. Mouth and tooth spray apparatus according to claim 1, wherein the free space is located along one side of the base and when the container is mounted on the base for use, it is located along the other side thereof.

5. Mouth and tooth spray apparatus according to claim 1 further comprising means for vertical storage of spray nozzles which are not in use in the base surface.

6. Mouth and tooth spray apparatus according to claim 1 wherein the appliance base has on its other side a receiving part for pushing the appliance base onto a wall bracket, and has on its end opposite the winding body a wall bracket identical to the first mentioned wall bracket, for pushing on a toothbrush charging appliance.

7. Mouth and tooth spray apparatus according to claim 1 further comprising a water pump, wherein an electric toothbrush is used as the drive for the water pump, the electric toothbrush being inserted upside down in a receptacle of the appliance base.

* * * * *